United States Patent
Wagner et al.

[11] Patent Number: 5,108,446
[45] Date of Patent: Apr. 28, 1992

[54] HIP JOINT PROSTHESIS

[75] Inventors: Heinz Wagner, Schwarzenbruck, Fed. Rep. of Germany; Roland Willi, Stadel, Switzerland

[73] Assignee: Sulzer Brothers Limited, Winterthur, Switzerland

[21] Appl. No.: 769,002

[22] Filed: Sep. 30, 1991

[30] Foreign Application Priority Data

Nov. 26, 1990 [CH] Switzerland .................. 03737/90

[51] Int. Cl.⁵ .......................... A61F 2/32; A61F 2/30
[52] U.S. Cl. ......................................... 623/22; 623/18
[58] Field of Search .................. 623/22, 23, 18, 16

[56] References Cited

U.S. PATENT DOCUMENTS 4,828,565 5/1989 Duthoit et al. ................... 623/22
4,955,917 9/1990 Karpf ................................. 623/22

FOREIGN PATENT DOCUMENTS 2615726 12/1988 European Pat. Off. ............. 623/18
0393543 10/1990 European Pat. Off. ............. 623/22
3446048 10/1985 Fed. Rep. of Germany ........ 623/22
2639822  6/1990 France ................................ 623/22

Primary Examiner—Ronald Frinks
Attorney, Agent, or Firm—Kenyon & Kenyon

[57] ABSTRACT

The hip joint prosthesis consists of two cups which are anchored together in the direction of the polar axes by a snap connection. The inner cup is made of cobalt alloy and outer cup of titanium. The outer cup carries a straddling dowel which projects into the bone tissue and which is subdivided into radially deflectable segments having sharp edges thereon. The inner cup has a shaped body which projects into the dowel and which is shaped so as to expand the deflectable segments upon rotation of the inner cup within the outer cup. Each dowel segment is provided with a notch to receive a corner of the shaped body so as to hold the body in a holding position in a snap-fit manner.

14 Claims, 1 Drawing Sheet

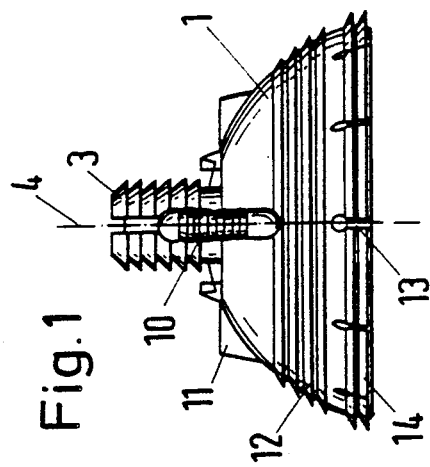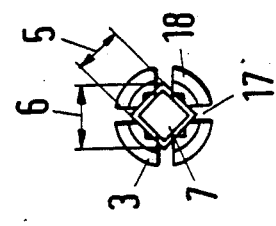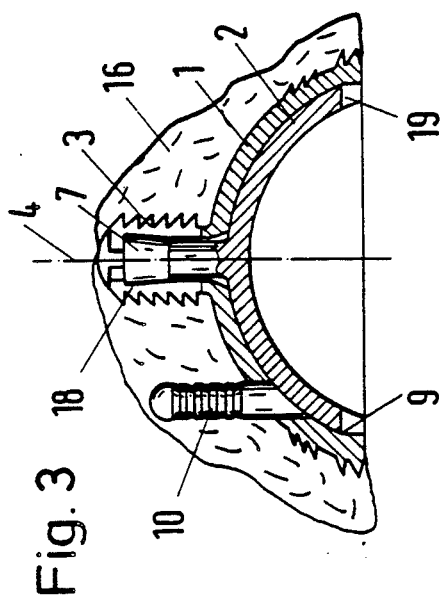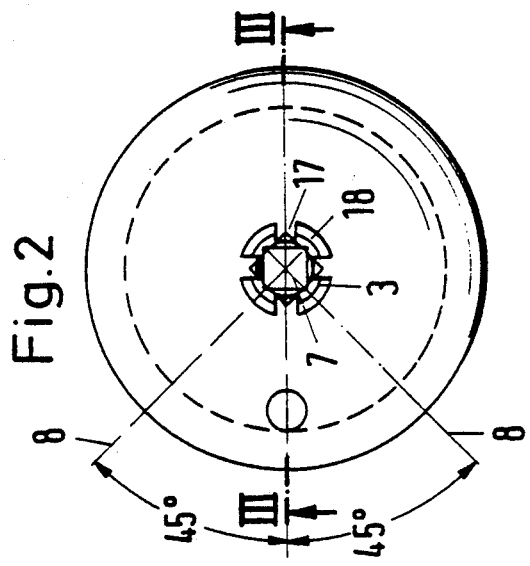

HIP JOINT PROSTHESIS

This invention relates to a hip joint prosthesis. More particularly, this invention relates to a hip joint prosthesis for embedding in a pelvis.

As is known, various types of hip joint sockets have been provided for implanting in a pelvis. For example, German Patent 34 46 048 describes a two-part metallic hip joint socket which exhibits a detachable clamp connection between two half-cups, i.e., hemispherical cups. As described, both hemispherical cups are in contact over fairly large areas with bone tissue and should therefore consist of tissue-compatible material. However, this restricts the choice of materials from which the cups can be made. Further, a primary anchorage is obtained with the use of supporting ribs and a drive-in sleeve. However, anchorage is dependent upon the adhesion of the bone tissue springing back upon driving in of the hemispherical cups. Thus, the state of the bone tissue which, particularly in the case of older patients, may not be regarded as being elastic, determines the quality of the primary anchorage.

Accordingly, it is an object of the invention to provide a hip joint prosthesis which can obtain a secure primary anchorage in a pelvis.

It is another object of the invention to provide a hip joint prosthesis of relatively simple construction which can be readily embedded in a pelvis.

Briefly, the invention provides a hip joint prosthesis comprised of an outer cup, for example of a cobalt alloy, and an inner cup, for example of titanium, which is rotatably mounted within the outer cup.

In accordance with the invention, the outer cup is provided with an outwardly extending dowel which is disposed on a polar axis of the outer cup and which is sub-divided into a plurality of radially deflectable segments. This straddling dowel is sized so as to project into the bone tissue of a pelvis. In addition, the inner cup is provided with a shaped body which extends on the polar axis of the prosthesis into the dowel and within the segments of the dowel. This body is further shaped to radially expand the segments of the dowel in response to rotation of the body within the dowel from a rest position to a holding position. For example, the body may be of polygonal shape having different diameters.

Each deflectable segment of the dowel is provided with a notch which faces the shaped body extending from the inner cup while the body itself has a plurality of corners or the like each of which is sized to snap into a respective notch in the holding position of the body. Each deflectable segment of the dowel is also provided with outwardly extending ribs or points having sharp edges for biting into bone tissue.

Initially, the hip joint prosthesis is pressed into a pelvis with the dowel penetrating into the pelvic bone tissue. Thereafter, the inner cup is rotated relative to the outer cup so that the shaped body radially expands the segments of the dowel causing the sharp edges on the segments to penetrate into the bone tissue.

One of the advantages of the prosthesis is that the segments of the dowel execute a predetermined anchoring motion transversely to the direction of introduction and engage in the bone tissue.

In order to prevent rotation of the outer cup within the pelvis, at least one guide pin may project from the outer cup in parallel to the dowel for embedding in a pelvis.

These and other objects and advantages of the invention will become more apparent from the following detailed description taken in conjunction with the accompanying drawings wherein:

FIG. 1 illustrates a side view of a hip joint prosthesis constructed in accordance with the invention;

FIG. 2 illustrates a plan view of the prosthesis of FIG. 1;

FIG. 3 illustrates a cross-sectional view taken on line III—III of FIG. 2; and

FIG. 4 illustrates a detailed view of the shaped body and deflectable segments of the dowel of the prosthesis.

Referring to FIGS. 1 and 3, the hip joint prosthesis is made of metal for insertion in bone tissue and consists of two cups 1, 2 which are anchored together in the direction of their polar axes 4, for example, by means of a snap-fit connection 9.

The outer cup 1 is made of titanium and has an outwardly extending straddling dowel 3 which is to project into bone tissue (see FIG. 3) and is disposed on the polar axis 4 of the cup 1. As illustrated, the dowel 3 is sub-divided into a plurality of radially deflectable segments 18. For example, the dowel 3 is composed of four parallel segments 18 which are separated by slits 17 (see FIG. 4). Also, each segment 18 is provided with plurality of outwardly directed teeth or sharp projections for penetrating into bone tissue.

The inner cup 2 is rotatable within the outer cup 1 and has a shaped body 7 which extends on the polar axis 4 into the dowel 3 and within the segments 18. As indicated in FIG. 3, the body 7, is integral with the inner cup 2 and is able to rotate inside the dowel 3. Further, the body 7 is shaped to radially expand the segments 18 of the dowel 3 in response to rotation of the body 7 within the dowel 3 from a rest position as shown in FIG. 4 to a holding position as shown in FIG. 2.

As indicated in FIG. 4, each segment 18 is provided with a notch facing the body 7 while the body 7 is provided with a plurality of corners each of which is sized to snap into a respective notch as indicated in FIG. 2 when in the holding position.

As shown in FIG. 1, the outer cup 1 is also provided with a guide pin 10 which projects from the cup 1 in parallel to the dowel 3 for embedding in a pelvis bone 16 in order to prevent rotation of the outer cup 1 therein. In addition, a plurality of spikes 11 and a plurality of annular members 12 with a cutting edge on each are provided on the outside of the outer cup 1 for anchoring in the bone tissue.

As also shown in FIG. 1, the outer cup 1 is provided with cuts or slits 13 in circumferentially spaced relation about the base of the cup so that spring-like tongues 14 are formed which can spring apart when the inner cup 2 is inserted into the outer cup 1 and thus serve to secure the inner cup 2 in the direction of the polar axis 4 by the snap connection 9.

Referring to FIG. 4, the shaped body 7 may be of polygonal shape, for example in the form of square. In this case, the width of one side 5 is greater than the diagonal 6 so that the body 7 has different "diameters". When in the rest position, the corners of the body 7 are disposed within the slits 17 of the dowel 3.

Referring to FIG. 2, after the inner cup 2 has been rotated relative to the outer cup 1, the shaped body 7 moves over an angle of 45° so as to place the corners of the shaped body 7 in the notches of the segments 18, i.e.

in the holding position. In this position, the dowel 3 has been spread by the body 7. At this time, the segments 18 are deflected radially outwardly of the polar axis 4 so as to become embedded in the bone tissue. Of note, the notches in the segments 18 ensure against an unintentional further twisting of the shaped body 7 within the dowel 3.

Referring to FIG. 3, as shown, the shaped body 7 is integral with the inner cup 2 which, in turn, is secured, through the snap connection 9, axially within the outer cup 1 so as to be able to turn in the outer cup 1. The inner cup 2 also has a plurality of recesses 19 in the base edge by which the inner cup 2 may be twisted with respect to the outer cup 1 by an auxiliary tool (not shown) in order to effect spreading of the segments 18 of the straddling dowel 3. The torque occurring during twisting is transmitted from the outer cup 1 to the bone tissue 16 by the dowel 3 and the guide pin 10 so that no additional loading arises upon the sharp-edged spikes 11 and annular members 12 pressed into the bone tissue. By spreading of the dowel segments 18, the outer cup 1 is anchored in the bone tissue 16 and secured. In this respect, the projections of the segments 18 dig transversely into the bone tissue 16 transversely of the polar axis 4 with the spreading motion.

In the premounted state, i.e. with the snap connection 9 snapped in, the two cups 1, 2 are pressed in the direction of the polar axis 4 into the premachined bone tissue 16 and the inner cup 2 is thereafter twisted with respect to the outer cup 1 until the corners of shaped body 7 snap into the notches of the deflectable segments 18 (see FIG. 2). The deflectable segments 18 are rounded towards the slits 17 so that they can be spread by the bearing areas of the shaped body 7. In the region of engagement, the shaped body 7 has a tapered surface at one end while each segment 18 has a tapered surface extending longitudinally of the polar axis 4 to mate with the tapered surface of the body 7. This is more particularly shown in FIG. 3. Thus, upon spreading of the dowel segments 18, the inner cup 1 is prevented from being loosened from the outer cup 2 in the axial direction should there be any possible play in the snap connection 9.

The pre-assembly of the two cups 1, 2 ensures that no foreign bodies, for example chips of bone, may become lodged between the bearing areas of the cups 1, 2. At the same time, solid primary anchoring is achieved without the bearing area inside the inner cup 2 exhibiting any gaps towards the head of the femur head to interrupt the lubricating film and pressure cushion to be formed thereat.

The invention thus provides a hip joint prosthesis which can be readily embedded in a pelvis with a secure primary anchorage taking place.

The invention further provides a hip joint prosthesis which can be embedded in a pelvis in a secure manner.

What is claimed is:

1. A hip joint prosthesis comprising
  an outer cup of titanium having an outwardly extending dowel disposed on a polar axis of said cup, said dowel being sub-divided into a plurality of radially deflectable segments; and
  an inner cup of cobalt alloy rotatably mounted within said outer cup and having a shaped body extending on said axis into said dowel and within said segments, said body being shaped to radially expand said segments in response to rotation of said body within said dowel from a rest position to a holding position.

2. A hip joint prosthesis as set forth in claim 1 wherein each segment has a notch facing said body and said body has a plurality of corners, each corner being sized to snap into a respective notch in said holding position of said body.

3. A hip joint prosthesis as set forth in claim 1 which further comprises a snap-fit connection between said cups for securing said cups together axially.

4. A hip joint prosthesis as set forth in claim 1 wherein said body is of polygonal shape.

5. A hip joint prosthesis as set forth in claim 1 which further comprises at least one guide pin projecting from said outer cup in parallel to said dowel for embedding in a pelvis to prevent rotation of said outer cup therein.

6. A hip joint prosthesis as set forth in claim 1 which further comprises at least one spike and at least one annular member with a cutting edge on said outer cup for anchoring in bone tissue.

7. A hip joint prosthesis as set forth in claim 1 wherein said body is integral with said inner cup.

8. A hip joint prosthesis as set forth in claim 7 wherein said body has a tapered surface at one end and each segment of said dowel has a tapered surface extending longitudinally of said polar axis and mating with said tapered surface of said body.

9. A hip joint prosthesis comprising
  an outer cup having an outwardly extending dowel disposed on a polar axis of said cup, said dowel being sub-divided into a plurality of radially deflectable segments; and
  an inner cup rotatably mounted within said outer cup and having a shaped body extending on said axis into said dowel and within said segments, said body being shaped to radially expand said segments in response to rotation of said body within said dowel from a rest position to a holding position.

10. A hip joint prosthesis as set forth in claim 9 wherein each segment has a notch facing said body and said body has a plurality of corners, each corner being sized to snap into a respective notch in said holding position of said body.

11. A hip joint prosthesis as set forth in claim 10 wherein said body is of polygonal shape.

12. A hip joint prosthesis as set forth in claim 9 which further comprises at least one guide pin projecting from said outer cup in parallel to said dowel for embedding in a pelvis to prevent rotation of said outer cup therein.

13. A hip joint prosthesis comprising
  an outer cup having an outwardly extending dowel disposed on a polar axis of said cup, said dowel being sub-divided into a plurality of radially deflectable segments, each segment having outwardly directed teeth thereon; and
  an inner cup rotatably mounted within said outer cup and having a polygonal shaped body extending on said axis into said dowel and within said segments, said body being shaped to radially expand said segments in response to rotation of said body within said dowel from a rest position to a holding position.

14. A hip joint prosthesis as set forth in claim 13 wherein each segment has a notch facing said body and said body has at least one corner sized to snap into a respective notch in said holding position of said body.

* * * * *